(12) United States Patent
Tanaka et al.

(10) Patent No.: US 8,084,044 B2
(45) Date of Patent: Dec. 27, 2011

(54) PSEUDOMONAS AERUGINOSA OUTER MEMBRANE PROTEIN PA0427

(75) Inventors: Jiro Tanaka, Yokohama (JP); Fukuichi Ohsawa, Yokohama (JP); Takafumi Okutomi, Tokyo (JP); Hiroshi Nagaso, Tokyo (JP); Masashi Kumagai, Yokohama (JP); Takahisa Suzuki, Yokohama (JP); Keiko Otsuka, Tokyo (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 12/225,821

(22) PCT Filed: Mar. 30, 2007

(86) PCT No.: PCT/JP2007/057107
§ 371 (c)(1),
(2), (4) Date: Sep. 30, 2008

(87) PCT Pub. No.: WO2007/114340
PCT Pub. Date: Oct. 11, 2007

(65) Prior Publication Data
US 2009/0117121 A1 May 7, 2009

(30) Foreign Application Priority Data
Mar. 30, 2006 (JP) .................................. 2006-095996

(51) Int. Cl.
*A61K 39/108* (2006.01)
(52) U.S. Cl. ............... 424/260.1; 424/234.1; 424/270.1; 530/387.1; 530/388.1
(58) Field of Classification Search ........................ None
See application file for complete search history.

(56) References Cited

U.S. PATENT DOCUMENTS
6,551,795 B1 * 4/2003 Rubenfield et al. .......... 435/69.1

FOREIGN PATENT DOCUMENTS
WO 2007/049770 5/2007

OTHER PUBLICATIONS

Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
Greenspan et al (Nature Biotechnology 7: 936-937, 1999).*
Chothia et al (The EMBO Journal, 1986, 5/4:823-26).*
Q. Zhao et al., "Contribution of Outer Membrane Efflux Protein OprM to Antibiotic Resistance in *Pseudomonas aeruginosa* Independent of MexAB", Antimicrobial Agents and Chemotherapy, Jul. 1998, vol. 42, No. 7, pp. 1682-1688.
N. Gotoh et al., "Characterization of the MexC-MexD-OprJ Multidrug Efflux System in Δ*mexA-mexB-oprM* Mutants of *Pseudomonas aeruginosa*", Antimicrobial Agents and Chemotherapy, Aug. 1998, vol. 42, No. 8, pp. 1938-1943.
A. Nakajima et al., "Localization of the Outer Membrane Subunit OprM of Resistance-Nodulation-Cell Division Family Multicomponent Efflux Pump in *Pseudomonas aeruginosa*", The Journal of Biological Chemistry, vol. 275, No. 39, pp. 30064-30068, Sep. 29, 2000.
I. Ziha-Zarifi et al., "In Vivo Emergence of Multidrug-Resistant Mutants of *Pseudomonas aeruginosa* Overexpressing the Active Efflux System MexA-MexB-OprM", Antimicrobial Agents and Chemotherapy, vol. 43, No. 2, pp. 287-291, Feb. 1999.
T. Nakae, "Yakuzai Haishutsu Pump Hatsugen ni yoru Tazai Taiseikabu no Jinsoku Kenshutsuho no Kaihatsu", Heisei 11 Nendo Kosei Kagaku Kenkyuhi Hojokin Saikin no Yakuzai Taisei Kiko no Bunshi Kaiseki to Taisei Kijobetsu Jinsoku Kenshutsuho no Kanrusu Kenkyu Kenkyu Hokokusho Heisei 12 Nen 4 Gatsu, pp. 79-82, Apr. 2000.
U. Baumann et al., "Recombinant OprF-OprI as a Vaccine Against *Pseudomonas aeruginosa* Infections", Vaccine, vol. 22, No. 7, pp. 840-847, 2004.
H. E. Gilleland et al., "Use of Synthetic Peptides to Identify Surface-Exposed, Linear B-Cell Epitopes Within Outer Membrane Protein F of *Pseudomonas aeruginosa*", Current Microbiology, vol. 31, No. 5, pp. 279-286, 1995.

* cited by examiner

*Primary Examiner* — Jennifer Graser
(74) *Attorney, Agent, or Firm* — Wenderoth, Lind & Ponack, L.L.P.

(57) ABSTRACT

An object of the present invention is to provide a protein or peptide antigen and an antibody against it, for use in the diagnosis, prevention, or treatment of diseases associated with *Pseudomonas aeruginosa*. According to the present invention, there is provided a protein or peptide derived from *Pseudomonas aeruginosa* outer membrane protein PA0427 and an antibody against it, for use in the diagnosis, prevention, or treatment of diseases associated with *Pseudomonas aeruginosa*.

7 Claims, 1 Drawing Sheet

FIG. 1

SEQUENCE LISTING

<160> NUMBER OF SEQ ID NOS: 18

<210> SEQ ID NO 1
<211> LENGTH: 1458
<212> TYPE: DNA
<213> ORGANISM: Pseudomonas aeruginosa

<400> SEQUENCE: 1

```
atgaaacggt ccttcctttc cctggcggta gccgctgtcg ttctgtccgg ctgctcgctg      60
atccccgact accagcgccc cgaggcgccg gtagccgcgg cctacccgca agggcaggcc     120
tacgggcaga acaccggcgc ggcggccgtt ccggccgccg acatcggctg gcgcgagttc     180
ttccgcgacc cgcagttgca gcaactgatc ggcgtggcgc tggaaaacaa ccgcgacctg     240
cgggtcgccg cgctgaacgt cgaggccttc cgggcgcagt accgcatcca gcgggccgac     300
ctgttcccgc ggatcggcgt ggacggtagc ggcacccgcc agcgtttgcc gggcgacctg     360
tcgaccaccg gcagtccggc gatttccagc cagtacgggg tgaccctggg cactaccgcc     420
tgggaactcg atctcttcgg ccgcctgcgc agcctgcgcg accaggccct ggagcagtac     480
ctggcgaccg aacaggcgca gcgcagcgcg cagaccaccc tggtggccag cgtggcgacc     540
gcctacctga cgctgaaggc cgaccaggcg cagttgcagc tgaccaagga cacctgggc     600
```

```
acctaccaga agagtttcga cctgacccag cgcagctacg acgtcggcgt cgcctccgcg    660
ctcgacctgc gccaggcgca gaccgccgtg aaggcgccc gcgcgaccct ggcgcagtac    720
acccgcctgg tagcccagga ccagaatgcg ctggtcctgc tgctgggctc cgggatcccg    780
gcgaacctgc cgcaaggcct gggcctggac cagaccctgc tgaccgaagt gccggcgggt    840
ctgccgtcgg acctgctgca acggcgcccg acatcctcg aggccgagca ccagctcatg    900
gctgccaacg ccagcatcgg cgccgcgcgc ggcgttct ccccgagcat cagcctgacc      960
gccaacgccg gcaccatgag ccgccaactg tccggcctgt cgacgccgg ttcgggttcc    1020
tggttgttcc agccgtcgat caacctgccg atcttcaccg ccggcagcct gcgtgccagc    1080
ctggactacg cgaagatcca aaggacatc aacgtcgcgc agtacgagaa ggcgatccag    1140
acggcgttcc aggaagtcgc cgacggcctg gccgcgcgcg gtaccttcac cgagcagttg    1200
caggcgcagc gcgatctggt caaggccagc gacgagtact accagctcgc cgacaagcgc    1260
tatcgcacgg gggtggacaa ctacctgacc ctgctcgacg cgcaacgctc gctgttcacc    1320
gcgcagcagc aactgatcac cgaccgcctc aatcagctga ccagcgaggt caacctgtac    1380
aaggccctcg gcggcggctg gaaccagcag accgtgaccc agcagcagac cgcgaagaag    1440
gaagatcccc aggcttga                                                 1458

<210> SEQ ID NO 2
<211> LENGTH: 678
<212> TYPE: DNA
<213> ORGANISM: Pseudomonas aeruginosa

<400> SEQUENCE: 2
cagcgtttgc cgggcgacct gtcgaccacc ggcagtccgg cgatttccag ccagtacggg    60
gtgaccctgg gcactaccgc ctgggaactc gatctcttcg ccgcctgcg cagcctgcgc    120
gaccaggccc tggagcagta cctggcgacc gaacaggcgc agcgcagcgc gcagaccacc    180
ctggtggcca gcgtggcgac cgcctacctg acgctgaagg ccgaccaggc gcagttgcag    240
ctgaccaagg acaccctggg cacctaccag aagagtttcg acctgaccca gcgcagctac    300
gacgtcggcg tcgcctccgc gctcgacctg cgccaggcgc agaccgccgt ggaaggcgcc    360
cgcgcgaccc tggcgcagta cacccgcctg gtagcccagg accagaatgc gctggtcctg    420
ctgctgggct ccgggatccc ggcgaacctg ccgcaaggcc tgggcctgga ccagaccctg    480
ctgaccgaag tgccggcggg tctgccgtcg gacctgctgc aacggcgccc ggacatcctc    540
gaggccgagc accagctcat ggctgccaac gccagcatcg gcgccgcgcg cggcgttc      600
ttcccgagca tcagcctgac cgccaacgcc ggcaccatga ccgccaact gtccggcctg    660
ttcgacgccg gttcgggt                                                 678

<210> SEQ ID NO 3
<211> LENGTH: 485
<212> TYPE: PRT
<213> ORGANISM: Pseudomonas aeruginosa

<400> SEQUENCE: 3

Met Lys Arg Ser Phe Leu Ser Leu Ala Val Ala Ala Val Val Leu Ser
 1               5                  10                  15

Gly Cys Ser Leu Ile Pro Asp Tyr Gln Arg Pro Glu Ala Pro Val Ala
                20                  25                  30

Ala Ala Tyr Pro Gln Gly Gln Ala Tyr Gly Gln Asn Thr Gly Ala Ala
            35                  40                  45

Ala Val Pro Ala Ala Asp Ile Gly Trp Arg Glu Phe Phe Arg Asp Pro
```

-continued

```
            50                  55                  60
Gln Leu Gln Gln Leu Ile Gly Val Ala Leu Glu Asn Asn Arg Asp Leu
 65                  70                  75                  80

Arg Val Ala Ala Leu Asn Val Glu Ala Phe Arg Ala Gln Tyr Arg Ile
                 85                  90                  95

Gln Arg Ala Asp Leu Phe Pro Arg Ile Gly Val Asp Gly Ser Gly Thr
            100                 105                 110

Arg Gln Arg Leu Pro Gly Asp Leu Ser Thr Thr Gly Ser Pro Ala Ile
            115                 120                 125

Ser Ser Gln Tyr Gly Val Thr Leu Gly Thr Thr Ala Trp Glu Leu Asp
130                 135                 140

Leu Phe Gly Arg Leu Arg Ser Leu Arg Asp Gln Ala Leu Glu Gln Tyr
145                 150                 155                 160

Leu Ala Thr Glu Gln Ala Gln Arg Ser Ala Gln Thr Thr Leu Val Ala
                165                 170                 175

Ser Val Ala Thr Ala Tyr Leu Thr Leu Lys Ala Asp Gln Ala Gln Leu
            180                 185                 190

Gln Leu Thr Lys Asp Thr Leu Gly Thr Tyr Gln Lys Ser Phe Asp Leu
            195                 200                 205

Thr Gln Arg Ser Tyr Asp Val Gly Val Ala Ser Ala Leu Asp Leu Arg
210                 215                 220

Gln Ala Gln Thr Ala Val Glu Gly Ala Arg Thr Leu Ala Gln Tyr
225                 230                 235                 240

Thr Arg Leu Val Ala Gln Asp Gln Asn Ala Leu Val Leu Leu Leu Gly
                245                 250                 255

Ser Gly Ile Pro Ala Asn Leu Pro Gln Gly Leu Gly Leu Asp Gln Thr
            260                 265                 270

Leu Leu Thr Glu Val Pro Ala Gly Leu Pro Ser Asp Leu Leu Gln Arg
            275                 280                 285

Arg Pro Asp Ile Leu Glu Ala Glu His Gln Leu Met Ala Ala Asn Ala
290                 295                 300

Ser Ile Gly Ala Ala Arg Ala Ala Phe Phe Pro Ser Ile Ser Leu Thr
305                 310                 315                 320

Ala Asn Ala Gly Thr Met Ser Arg Gln Leu Ser Gly Leu Phe Asp Ala
                325                 330                 335

Gly Ser Gly Ser Trp Leu Phe Gln Pro Ser Ile Asn Leu Pro Ile Phe
            340                 345                 350

Thr Ala Gly Ser Leu Arg Ala Ser Leu Asp Tyr Ala Lys Ile Gln Lys
            355                 360                 365

Asp Ile Asn Val Ala Gln Tyr Glu Lys Ala Ile Gln Thr Ala Phe Gln
370                 375                 380

Glu Val Ala Asp Gly Leu Ala Ala Arg Gly Thr Phe Thr Glu Gln Leu
385                 390                 395                 400

Gln Ala Gln Arg Asp Leu Val Lys Ala Ser Asp Glu Tyr Tyr Gln Leu
                405                 410                 415

Ala Asp Lys Arg Tyr Arg Thr Gly Val Asp Asn Tyr Leu Thr Leu Leu
            420                 425                 430

Asp Ala Gln Arg Ser Leu Phe Thr Ala Gln Gln Leu Ile Thr Asp
            435                 440                 445

Arg Leu Asn Gln Leu Thr Ser Glu Val Asn Leu Tyr Lys Ala Leu Gly
450                 455                 460

Gly Gly Trp Asn Gln Gln Thr Val Thr Gln Gln Thr Ala Lys Lys
465                 470                 475                 480
```

```
Glu Asp Pro Gln Ala
            485

<210> SEQ ID NO 4
<211> LENGTH: 226
<212> TYPE: PRT
<213> ORGANISM: Pseudomonas aeruginosa

<400> SEQUENCE: 4

Gln Arg Leu Pro Gly Asp Leu Ser Thr Thr Gly Ser Pro Ala Ile Ser
1               5                   10                  15

Ser Gln Tyr Gly Val Thr Leu Gly Thr Thr Ala Trp Glu Leu Asp Leu
            20                  25                  30

Phe Gly Arg Leu Arg Ser Leu Arg Asp Gln Ala Leu Glu Gln Tyr Leu
        35                  40                  45

Ala Thr Glu Gln Ala Gln Arg Ser Ala Gln Thr Thr Leu Val Ala Ser
    50                  55                  60

Val Ala Thr Ala Tyr Leu Thr Leu Lys Ala Asp Gln Ala Gln Leu Gln
65                  70                  75                  80

Leu Thr Lys Asp Thr Leu Gly Thr Tyr Gln Lys Ser Phe Asp Leu Thr
                85                  90                  95

Gln Arg Ser Tyr Asp Val Gly Val Ala Ser Ala Leu Asp Leu Arg Gln
            100                 105                 110

Ala Gln Thr Ala Val Glu Gly Ala Arg Ala Thr Leu Ala Gln Tyr Thr
        115                 120                 125

Arg Leu Val Ala Gln Asp Gln Asn Ala Leu Val Leu Leu Leu Gly Ser
    130                 135                 140

Gly Ile Pro Ala Asn Leu Pro Gln Gly Leu Gly Leu Asp Gln Thr Leu
145                 150                 155                 160

Leu Thr Glu Val Pro Ala Gly Leu Pro Ser Asp Leu Leu Gln Arg Arg
                165                 170                 175

Pro Asp Ile Leu Glu Ala Glu His Gln Leu Met Ala Ala Asn Ala Ser
            180                 185                 190

Ile Gly Ala Ala Arg Ala Ala Phe Phe Pro Ser Ile Ser Leu Thr Ala
        195                 200                 205

Asn Ala Gly Thr Met Ser Arg Gln Leu Ser Gly Leu Phe Asp Ala Gly
    210                 215                 220

Ser Gly
225

<210> SEQ ID NO 5
<211> LENGTH: 14
<212> TYPE: PRT
<213> ORGANISM: Pseudomonas aeruginosa

<400> SEQUENCE: 5

Thr Arg Gln Arg Leu Pro Gly Asp Leu Ser Thr Thr Gly Ser
1               5                   10

<210> SEQ ID NO 6
<211> LENGTH: 15
<212> TYPE: PRT
<213> ORGANISM: Pseudomonas aeruginosa

<400> SEQUENCE: 6

Ala Gly Thr Met Ser Arg Gln Leu Ser Gly Leu Phe Asp Ala Gly
1               5                   10                  15

<210> SEQ ID NO 7
```

```
<211> LENGTH: 25
<212> TYPE: DNA
<213> ORGANISM: Artificial Sequence
<220> FEATURE:
<223> OTHER INFORMATION: primer

<400> SEQUENCE: 7
caaggacgag gcgtccaagc agcag                                              25

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
cgcactgctg acccgcaacc gctaa                                              25

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
cgcagttgca gcaactgatc                                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
acctaccaga agagtttcga                                                    20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tggttgttcc agccgtcgat                                                    20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ccgaagagat cgagttccca                                                    20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
```
acatcggctg gcgcgagttc                                            20

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
gactccatgg gccagcgttt gccgggcg                                   28

<210> SEQ ID NO 15
<211> LENGTH: 31
<212> TYPE: DNA
<213> ORGANISM: Artificial Sequence
<220> FEATURE:
<223> OTHER INFORMATION: primer

<400> SEQUENCE: 15
aagtctgcag tcaacccgaa ccggcgtcga a                               31

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
taatacgact cactataggg                                            20

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
aagtagatct caacccgaac cggcgtcgaa                                 30

<210> SEQ ID NO 18
<211> LENGTH: 16
<212> TYPE: PRT
<213> ORGANISM: Artificial Sequence
<220> FEATURE:
<223> OTHER INFORMATION: synthetic peptide

<400> SEQUENCE: 18

Ala Gly Thr Met Ser Arg Gln Leu Ser Gly Leu Phe Asp Ala Gly Cys
1               5                   10                  15

PSEUDOMONAS AERUGINOSA OUTER MEMBRANE PROTEIN PA0427

This application is a U.S. national stage of International Application No. PCT/JP2007/057107 filed Mar. 30, 2007.

TECHNICAL FIELD

The present invention relates to a protein antigen or a peptide antigen derived from a *Pseudomonas aeruginosa* outer membrane protein PA0427, and an antibody against the antigen. The present invention also relates to a vaccine composition comprising the antigen. The present invention further relates to a pharmaceutical composition, a diagnostic agent for a *Pseudomonas aeruginosa* infection, and a kit for detecting *Pseudomonas aeruginosa*, comprising the antibody.

BACKGROUND ART

*Pseudomonas aeruginosa*, which is a gram negative *bacillus* universally distributed in natural environments such as soil and water, causes serious lethal infections resistant to therapy. Its main targets are compromised patients with attenuated host defense functions generally called compromised hosts including burned, organ-transplanted, and cancer patients. *Pseudomonas aeruginosa* is a main causative bacterium of hospital infections. Furthermore, lung infections caused by this bacterium are lethal to cystic fibrosis patients. An antimicrobial agent having anti-*Pseudomonas aeruginosa* activity is mainly administered to these patients, while many cases do not sufficiently receive a therapeutic effect due to the drug resistance of *Pseudomonas aeruginosa*. Alternatively, vaccines or antibodies against *Pseudomonas aeruginosa* have also been studied for a long time. However, methods directly using inactivated forms of the bacterium had such a disadvantage that various types of vaccines or antibodies must be prepared depending on the different serotypes of *Pseudomonas aeruginosa*.

In such a situation, the prevention or treatment of a *Pseudomonas aeruginosa* infection using passive immunity or active immunity with a *Pseudomonas aeruginosa* protein having a common amino acid sequence among *Pseudomonas aeruginosa* strains has been expected. For example, a recombinant protein in which portions of outer membrane proteins OprF and OprI have been fused with each other (Japanese Patent Laid-Open Publication No. 245699/1996), and a type IV pilin protein (WO2004/099250) have been known as applications of such a *Pseudomonas aeruginosa* protein to vaccines.

Moreover, an anti-type IV pilin antibody (WO2004/099250), an anti-PA1706 (or PcrV) antibody (U.S. Pat. Nos. 6,309,651 and 6,827,935), and the like have been reported for antibody drugs targeting a *Pseudomonas aeruginosa* protein.

However, a bacterial protein commonly possessed among clinical isolates of *Pseudomonas aeruginosa*, which exhibit diverse serotypes, can be applied as a "*Pseudomonas aeruginosa* common antigen" to the prevention, diagnosis, or treatment of a *Pseudomonas aeruginosa* infection and as such, has always been demanded.

It has been reported that a PA0427 (also known as OprM) protein encoded by a PA0427 (or oprM) gene is an outer membrane protein that constitutes secretion apparatuses of homoserine lactone serving as a signal molecule in *Pseudomonas aeruginosa* quorum sensing and, as an outer membrane protein that constitutes multicomponent xenobiotic efflux pumps for ejecting tetracycline, chloramphenicol, new quinolone, and β-lactam antibiotics, is also directly involved in resistance to these antibiotics (Journal of Bacteriology, 1998, 180, 5443-5447; and Antimicrobial Agents and Chemotherapy, 1995, 39, 1948-1953). Moreover, x-ray crystallographic structure analysis has been conducted on its three-dimensional structure, showing a three-dimensional structure with four outer membrane-spanning regions (Journal of Biological Chemistry, 2004, 279, 52816-52819). On the other hand, it has also been reported in animal experiments that pathogenicity is significantly reduced in *Pseudomonas aeruginosa* deficient in mexA-mexB-oprM operon encoding a xenobiotic efflux pump containing the protein, compared with wild strains, whereas pathogenicity is not reduced in variants deficient only in the PA0427 gene (Journal of Experimental Medicine, 2002, 196, 109-118). It has further been reported that an antiserum obtained by immunization with the protein is used as a reagent for detecting the protein in immunoblot (FEMS Microbiology Letters, 1994, 122, 267-274). However, anti-*Pseudomonas aeruginosa* drugs targeting the PA0427 protein have been unknown. Moreover, it has been unknown that the protein is used as a vaccine component, and that an antibody composition produced therefrom is used as a therapeutic or diagnostic agent for a *Pseudomonas aeruginosa* infection.

SUMMARY OF THE INVENTION

The present inventors have attempted to identify a novel and useful "*Pseudomonas aeruginosa* common antigen" from *Pseudomonas aeruginosa* outer membrane proteins. After various studies, the present inventors have found by GeneChip analysis that a gene encoding a PA0427 (also known as OprM) protein present in the outer membrane of *Pseudomonas aeruginosa* is constantly expressed regardless of the presence or absence of human sera (Example 1). The present inventors have also found by gene analysis on 95 clinical isolates of *Pseudomonas aeruginosa* that 2 putative extracellular regions of the PA0427 protein have no detectable amino acid mutation and are completely conserved (Example 2). The present inventors have further confirmed that an antiserum or antibody obtained by immunization with a PA0427 recombinant protein or a peptide containing each putative extracellular region binds to the PA0427 protein (Examples 7 and 8), that the antibody has opsonic activity (Example 9), and that the antibody exhibits potent protective effect against infections on *Pseudomonas aeruginosa*-infected model mice (Examples 11 to 13). The present invention is based on these findings.

An object of the present invention is to provide a protein antigen or a peptide antigen used as a vaccine composition which has an ability to substantially prevent or treat a *Pseudomonas aeruginosa* infection and can respond to the diversity of clinical isolates derived from patients with a *Pseudomonas aeruginosa* infection, or to provide an antibody against the antigen.

According to the present invention, there is provided an antigen composition comprising a protein antigen or a peptide antigen which can induce the production of an antibody against a *Pseudomonas aeruginosa* PA0427 protein.

According to the present invention, there is provided a protein selected from the group consisting of (hereinafter referred to as a "protein according to the present invention"):
(i) a protein comprising the amino acid sequence of SEQ ID NO: 4;
(ii) a protein which comprises an amino acid sequence of SEQ ID NO: 4 in which one or more amino acids are deleted, substituted, inserted, or added, and which is functionally equivalent to a protein consisting of the amino acid sequence of SEQ ID NO: 4;
(iii) a protein which is encoded by a polynucleotide which hybridizes under stringent conditions to a polynucleotide which encodes the amino acid sequence of SEQ ID NO: 4, and which is functionally equivalent to a protein consisting of the amino acid sequence of SEQ ID NO: 4; and
(iv) a protein which comprises an amino acid sequence having 70% or more identity with the amino acid sequence of SEQ ID NO: 4, and which is functionally equivalent to a protein consisting of the amino acid sequence of SEQ ID NO: 4.

According to the present invention, there is provided a peptide comprising the amino acid sequence of SEQ ID NO: 5, or an amino acid sequence of SEQ ID NO: 5 which contains one to several conservative substitutions (hereinafter referred to as a "peptide of a first embodiment according to the present invention").

According to the present invention, there is provided a peptide comprising the amino acid sequence of SEQ ID NO: 6, or an amino acid sequence of SEQ ID NO: 6 which contains one to several conservative substitutions (hereinafter referred to as a "peptide of a second embodiment according to the present invention") (hereinafter, the peptide of the first embodiment according to the present invention and the peptide of the second embodiment according to the present invention are occasionally collectively referred to as "peptide(s) according to the present invention").

According to the present invention, there is provided an antigen composition comprising the protein according to the present invention, or the peptide according to the present invention (hereinafter, this antigen composition, and the antigen composition comprising a protein antigen or a peptide antigen which can induce the production of an antibody against a Pseudomonas aeruginosa PA0427 protein are collectively referred to as "antigen composition(s) according to the present invention").

According to the present invention, there is provided a vaccine composition for use in the prevention or treatment of diseases associated with Pseudomonas aeruginosa, comprising the antigen composition according to the present invention, and optionally one or more pharmaceutically acceptable carriers, diluents, and/or adjuvants.

According to the present invention, there is provided an antibody against a Pseudomonas aeruginosa PA0427 protein or a portion thereof, or a functional fragment thereof (hereinafter referred to as an "antibody according to the present invention").

According to the present invention, there is provided a hybridoma deposited under the accession No. FERM BP-10782.

According to the present invention, there is provided a pharmaceutical composition for use in the prevention or treatment of diseases associated with Pseudomonas aeruginosa, comprising the antibody according to the present invention, and optionally one or more pharmaceutically acceptable carriers and/or diluents.

According to the present invention, there is provided a diagnostic agent for a Pseudomonas aeruginosa infection, comprising the antibody according to the present invention.

According to the present invention, there is provided a kit for detecting Pseudomonas aeruginosa, comprising the antibody according to the present invention.

The present invention provides a vaccine composition and a polyclonal antibody or a monoclonal antibody which have an ability to substantially prevent or treat a Pseudomonas aeruginosa infection and further respond to the diversity of clinical isolates derived from patients with a Pseudomonas aeruginosa infection. They may be applied to a preventive or therapeutic agent for a Pseudomonas aeruginosa infection, or a diagnostic agent for a Pseudomonas aeruginosa infection.

Furthermore, the antibody according to the present invention binds to the extracellular regions of the PA0427 protein present in the outer membrane of or extracellularly present in Pseudomonas aeruginosa. In addition, it is estimated that these regions are exceedingly highly conservative among strains regardless of serotypes etc., and react with diverse clinical isolates. Therefore, the antibody according to the present invention is expected to have a high therapeutic effect on a Pseudomonas aeruginosa infection.

DETAILED DESCRIPTION OF THE INVENTION

[PA0427 Protein]

A PA0427 protein is an outer membrane PA0427 protein derived from Pseudomonas aeruginosa. The amino acid sequence of the protein and the nucleotide sequence of a polynucleotide encoding the protein are described in SEQ ID NO: 3 and SEQ ID NO: 1, respectively.

In this context, based on secondary structure and three-dimensional structure information about the Pseudomonas aeruginosa PA0427 (OprM) protein (J. Biol. Chem., 2004, 279, 52816-52819) and three-dimensional structure information about an E. coli TolC protein (Nature, 2000, 405, 914-919), it was estimated that a nucleotide sequence of nucleotides 340 to 1017 in 1458 nucleotides as an amino acid coding region of the nucleotide sequence of SEQ ID NO: 1 encodes a cell surface-exposed portion of the PA0427 protein (SEQ ID NO: 2).

The cell surface-exposed portion of the PA0427 protein is a protein selected from the group consisting of:
(i) a protein comprising the amino acid sequence of SEQ ID NO: 4;
(ii) a protein which comprises an amino acid sequence of SEQ ID NO: 4 in which one or more amino acids are deleted, substituted, inserted, or added, and which is functionally equivalent to a protein consisting of the amino acid sequence of SEQ ID NO: 4;
(iii) a protein which is encoded by a polynucleotide which hybridizes under stringent conditions to a polynucleotide which encodes the amino acid sequence of SEQ ID NO: 4, and which is functionally equivalent to a protein consisting of the amino acid sequence of SEQ ID NO: 4; and
(iv) a protein which comprises an amino acid sequence having 70% or more identity with the amino acid sequence of SEQ ID NO: 4, and which is functionally equivalent to a protein consisting of the amino acid sequence of SEQ ID NO: 4.

In the present specification, the expression "one or more amino acids are deleted, substituted, inserted, or added" means that the modification has been carried out according to well-known technical methods such as site-directed mutagenesis, or by substitution of a plurality number of amino acids to an extent of being naturally generated. The number of amino acids to be modified may be preferably 1 to 50, more preferably 1 to 30, further more preferably 1 to 10, still further more preferably 1 to 5, and most preferably 1 or 2.

The modified amino acid sequence of the PA0427 protein can preferably be an amino acid sequence of SEQ ID NO:4 having one or more (preferably, one to several, or 1, 2, 3, or 4) conservative substitutions in the amino acid sequence.

In the present specification, the term "conservative substitution" means that one or more amino acid residues are substituted with other chemically similar amino acid residues. Examples of such conservative substitution include a case where a certain hydrophobic residue is substituted with another hydrophobic residue, and a case where a certain polar residue is substituted with another polar residue having the same electric charge. For every type of amino acids, functionally similar amino acids which can be substituted in such a manner are known in the present technical field. Examples of nonpolar (hydrophobic) amino acids include alanine, valine, isoleucine, leucine, proline, tryptophan, phenylalanine, and methionine. Examples of polar (neutral) amino acids include glycine, serine, threonine, tyrosine, glutamine, asparagine, and cysteine. Examples of positively charged (basic) amino acids include arginine, histidine, and lysine. Examples of negatively charged (acidic) amino acids include aspartic acid and glutamic acid.

In the present specification, the term "under stringent conditions" means conditions wherein a membrane washing procedure after hybridization is carried out at a high temperature in a solution having a low salt concentration. Such washing conditions can be, for example, 0.5×SSC (1×SSC: 15 mM trisodium citrate and 150 mM sodium chloride) at 60° C. for 15 minutes, and preferably 0.5×SSC, 0.1% SDS at 60° C. for 15 minutes.

Hybridization can be carried out in accordance with a known method. In the case of using a commercially available library, hybridization can be carried out according to the method described in instructions included therewith.

In the present specification, the term "identity" regarding nucleotide sequences or amino acid sequences means the degree of coincidence between the compared sequences in terms of nucleotide residues or amino acid residues that constitute such sequences. The numerical value of such "identity" shown in the present specification may be calculated using a homology search program known to persons skilled in the art. For example, such a numerical value as identity can easily be calculated using a default (initialization) parameter in FASTA or BLAST.

An amino acid sequence having 70% or more identity with the amino acid sequence of SEQ ID NO: 4 can be an amino acid sequence having preferably 80% or more, more preferably 85% or more, further more preferably 90% or more, still further more preferably 95% or more, particularly preferably 98% or more, and most preferably 99% or more identity with the aforementioned amino acid sequence.

In the present invention, if the amino acid sequence of SEQ ID NO: 4 is given, a nucleotide sequence encoding it can easily be determined. Thus, various nucleotide sequences encoding the amino acid sequence of SEQ ID NO: 4 can be selected.

Accordingly, a polynucleotide encoding a protein comprising the amino acid sequence of SEQ ID NO: 4 means not only a part of or the entire DNA sequence of SEQ ID NO: 2 but also a DNA sequence encoding the same amino acids, which has a codon having a degeneracy relationship therewith as a DNA sequence. The present invention further includes an RNA sequence corresponding to such a DNA sequence.

A preferred example of the polynucleotide encoding a protein comprising the amino acid sequence of SEQ ID NO: 4 includes a polynucleotide comprising the nucleotide sequence of SEQ ID NO: 2.

In the present specification, whether or not a certain protein is functionally equivalent to the protein consisting of the amino acid sequence of SEQ ID NO: 4 can be determined by evaluating a biological phenomenon or functions associated with the expression of the protein consisting of the amino acid sequence of SEQ ID NO: 4. For example, it can be determined by allowing the certain protein to express by genetic recombination technique and then evaluating whether or not an antibody against the PA0427 protein can be prepared.

Since the protein according to the present invention is exposed on the cell surface of *Pseudomonas aeruginosa*, the protein can be used as an antigen for preparing an antibody against *Pseudomonas aeruginosa* (protein antigen).

In the cell surface-exposed portion of the PA0427 protein, the following two portions having no detectable amino acid mutation (hereinafter referred to as putative extracellular regions) were identified:
a peptide comprising the amino acid sequence of SEQ ID NO: 5, or an amino acid sequence of SEQ ID NO: 5 which contains one to several conservative substitutions; and
a peptide comprising the amino acid sequence of SEQ ID NO: 6, or an amino acid sequence of SEQ ID NO: 6 which contains one to several conservative substitutions.

Since the peptides according to the present invention are exposed on the cell surface of *Pseudomonas aeruginosa* and conserved in *Pseudomonas aeruginosa*, the peptides can be used as an antigen for preparing an antibody against *Pseudomonas aeruginosa* (peptide antigen).

The peptides were confirmed to have no detectable amino acid mutation in a large number of clinical isolates of *Pseudomonas aeruginosa* and as such, are advantageous in that they are useful as a *Pseudomonas aeruginosa* common antigen.

For the peptides according to the present invention, a blocking group may be added to the N- or C-terminals thereof, for example, so as to prevent aggregation attributed to electric charges. Acetylation and amidation were often used for the N- and C-terminals, respectively, but not limited to these. The peptides according to the present invention can be modified, for example, by adding a cysteine residue thereto, so as to enhance binding with a spacer.

DMS (dimethyl suberimidate), DMA (Dimethyl adipimidate), Sulfo-SMCC (Sulfosuccinimidyl-4-[N-maleimidomethyl]cyclohexane-1-carboxylate), MBS (m-Maleimidobenzoyl-N-hydroxysuccinimide ester), Sulfo-MBS or the like is generally used as the spacer, but not limited to this. A compound functioning as a spacer can be used.

For the peptides according to the present invention, carrier proteins such as bovine serum albumin (BSA), ovalbumin (OVA), human serum albumin (HSA), or keyhole limpet hemocyanin (KLH) can be used as carriers, but not limited to these.

[Antigen Composition]

The protein according to the present invention or the peptides according to the present invention can be used as a protein antigen or a peptide antigen. Thus, according to the present invention, there is provided an antigen composition comprising the protein antigen or the peptide antigen which can induce the production of an antibody against a *Pseudomonas aeruginosa* outer membrane PA0427 protein.

In this context, the protein antigen or the peptide antigen can preferably be used by purifying the protein according to the present invention or the peptides according to the present invention according to a method well known to persons skilled in the art.

In the present specification, the term "antigen composition" may be a composition consisting of only the protein antigen or the peptide antigen, or a composition comprising such an antigen and other components.

According to the present invention, there is provided an antigen composition comprising a protein antigen or a peptide antigen which can induce the production of an antibody against a *Pseudomonas aeruginosa* PA0427 protein.
[Vaccine Composition]

The antigen compositions according to the present invention can be used as a vaccine. Thus, according to the present invention, there is provided a vaccine composition comprising an antigen composition which can induce the production of an antibody against a *Pseudomonas aeruginosa* outer membrane PA0427 protein.

According to the present invention, a vaccine composition for use in the prevention or treatment of diseases associated with *Pseudomonas aeruginosa*, comprising the antigen composition according to the present invention, and optionally one or more pharmaceutically acceptable carriers, diluents, and/or adjuvants can be prepared.

The carriers used in the vaccine composition according to the present invention are selected based on the mode and route of administration, and actual standard drug formulation and may be, for example, carrier proteins (e.g., bovine serum albumin (BSA), ovalbumin (OVA), human serum albumin (HSA), and keyhole limpet hemocyanin (KLH)), solubilizers (e.g., ethanol, polysorbate, and Cremophor EL™), isotonic agents, preservatives, antioxidants, excipients (e.g., lactose, starch, crystalline cellulose, mannitol, maltose, calcium hydrogen phosphate, light anhydrous silicic acid, and calcium carbonate), binders (e.g., starch, polyvinylpyrrolidone, hydroxypropylcellulose, ethylcellulose, carboxymethylcellulose, and gum arabic), lubricants (e.g., magnesium stearate, talc, and hydrogenated oil), and stabilizers (e.g., lactose, mannitol, maltose, polysorbate, macrogol, and polyoxyethylene hydrogenated castor oil). Glycerin, dimethylacetamide, 70% sodium lactate, a surfactant, or a basic substance (e.g., sodium hydroxide, ethylenediamine, ethanolamine, sodium bicarbonate, arginine, meglumine, or trisaminomethane), etc. may be added, if necessary.

Specifically, the peptides according to the present invention can be coupled to a known KLH solution (Calbiotec, 125 mg is dissolved per ml of a 50% glycerol solution) as a carrier protein, so as to enhance the antigenicity of the vaccine composition according to the present invention.

The diluents used in the vaccine composition according to the present invention are selected based on the mode and route of administration, and actual standard drug formulation. Examples of the diluents include water, a saline, a phosphate-buffered saline, and a bicarbonate solution.

The adjuvants used in the vaccine composition according to the present invention are selected based on the mode and route of administration, and actual standard drug formulation. Examples of the adjuvants include cholera toxin, *E. coli* heat-labile enterotoxin (LT), liposome, and an immunostimulating complex (ISCOM).

An administration route may differ depending on the age, body weight, sex, and general health of a recipient at risk of a *Pseudomonas aeruginosa* infection, but administration can be carried out by any of oral administration and parenteral administration (e.g., intravenous injection, intraarterial injection, and local administration) routes. Among them, parenteral administration is preferable.

The dosage form for oral administration and parenteral administration and the preparation method thereof are well known to persons skilled in the art. The dosage form for oral administration and parenteral administration can be prepared by a conventional process, for example, by mixing the antigen compositions according to the present invention, for example, with the aforementioned pharmaceutically acceptable carriers.

Examples of a dosage form for oral administration include solid and liquid dosage forms such as a solution, a tablet, a granule, a powder, or a capsule.

Examples of a dosage form for parenteral administration include a solution, a suspension, an ointment, a cream, a suppository, an ophthalmic agent, nasal drops, and ear drops.

If the sustained release of the present preparation is desired, a biodegradable polymer (e.g., poly-D,L-lactide-co-glycoside or polyglycoside) can be added as a bulk matrix (see e.g., U.S. Pat. Nos. 5,417,986, 4,675,381, and 4,450,150).

In the case of oral administration, a flavoring agent and a coloring agent can also be added.

Appropriate pharmaceutical carriers and diluents and the like, and pharmaceutical necessities for use thereof are described in Remington's Pharmaceutical Sciences.

A dose of the vaccine composition according to the present invention is determined by the present inventor based on the type of a vaccine antigen, the possibility of administration of the present antigen in combination with adjuvants, the type of the adjuvants coadministered therewith, the mode and frequency of administration, and a desired effect (e.g., a preventive or therapeutic effect), and may be generally 1 µg/dose to 100 mg/dose per adult. When the present vaccine is administered with adjuvants, the dose may be generally 1 ng/dose to 1 mg/dose per adult. Such a dose may be administered several times according to decision of the present inventor, as necessary. For example, initial vaccination and subsequent 3 booster vaccinations at 1-week intervals can be carried out. Alternatively, a booster injection and a second booster injection can be carried out on the 8th to 12th week and 16th to 20th week, respectively, from the first immunization, using the same formulations.
[Antibody]

The antibody according to the present invention can recognize a *Pseudomonas aeruginosa* outer membrane PA0427 protein or a portion thereof, and bind to the *Pseudomonas aeruginosa*.

According to the present invention, there is provided an antibody according to the present invention or a functional fragment thereof, wherein the portion of the *Pseudomonas aeruginosa* PA0427 protein is a cell surface-exposed portion of the *Pseudomonas aeruginosa* PA0427 protein.

According to the present invention, there is provided an antibody according to the present invention, wherein the portion of the *Pseudomonas aeruginosa* PA0427 protein is the protein according to the present invention (hereinafter referred to as an "antibody of a first embodiment according to the present invention").

According to the present invention, there is provided an antibody according to the present invention, wherein the portion of the *Pseudomonas aeruginosa* PA0427 protein is the peptide of the first embodiment according to the present invention (hereinafter referred to as an "antibody of a second embodiment according to the present invention").

According to the present invention, there is provided an antibody according to the present invention, wherein the portion of the *Pseudomonas aeruginosa* PA0427 protein is the peptide of the second embodiment according to the present invention (hereinafter referred to as an "antibody of a third embodiment according to the present invention").

Such an antibody includes an antibody that recognizes the protein according to the present invention and binds to the

*Pseudomonas aeruginosa*. It also includes an antibody that recognizes the peptide according to the present invention.

The antibody according to the present invention is preferably obtained by immunizing an experimental animal with an antigen composition comprising the purified protein antigen or peptide antigen according to the present invention, which is administered in an amount that can induce the antibody. Such an antibody can be used as a pure antibody by collecting blood from the heart or artery, separating antisera therefrom, and purifying the obtained antisera.

The antibody according to the present invention includes: a polyclonal antibody or monoclonal antibody obtained by using the PA0427 protein or peptide as an antigen and immunizing a mammal such as a mouse with the aforementioned antigen (which includes a monoclonal antibody produced by a hybridoma that produces the monoclonal antibody of the present invention); a chimeric antibody and a humanized antibody prepared by genetic recombination technique; and a human antibody prepared using a human antibody-producing transgenic animal or the like.

When the antibody according to the present invention is administered as a medicament to a human, a human antibody is preferably used in terms of reducing side effects.

The "human antibody" means an antibody wherein all regions are derived from humans. The human antibody according to the present invention can be prepared using a method well known to persons skilled in the art (see e.g., Intern. Rev. Immunol, 1995, 13, 65-93; J. Mol. Biol, 1991, 222, 581-597; Japanese Patent Laid-Open Publication No. 146194/1998; Japanese Patent Laid-Open Publication No. 155492/1998; Japanese Patent No. 2938569; Japanese Patent Laid-Open Publication No. 206387/1999; Japanese Patent Laid-Open Publication No. 509612/1996; and Japanese Patent Laid-Open Publication No. 505107/1999).

The "humanized antibody" is an antibody prepared by transplanting only the gene sequence of the antigen-binding site (CDR; complementarity determining region) of a mouse antibody into a human antibody gene (CDR grafting). The humanized antibody according to the present invention can be prepared using a method well known to persons skilled in the art (see e.g., EP239400 and WO90/07861).

The "chimeric antibody" is an antibody prepared by ligating the variable region of a certain antibody to the constant region of an antibody of different species therefrom. Specifically, a mouse is immunized with an antigen, and an antibody variable region (V region) that binds to the antigen is cut out of the gene of the mouse monoclonal antibody. The thus obtained V region is then allowed to bind to an antibody constant region (C region) gene derived from human bone marrow, so as to prepare a chimeric antibody. The chimeric antibody according to the present invention can be prepared using a method well known to persons skilled in the art (see e.g., Japanese Patent Laid-Open Publication No: 280387/1996 and U.S. Pat. Nos. 4,816,397, 4,816,567, and 5807715).

The monoclonal antibody according to the present invention can be prepared using a method well known to persons skilled in the art (see e.g., Antibodies: A Laboratory Manual, Ed Harlow and David Lane, Cold Spring Harbor Laboratory (1988); Experimental Manual for Monoclonal Antibody, edited by Sakuji Toyama et al., Kodansha, (1987); and Monoclonal Antibody: Hybridoma and ELISA, edited by Tatsuo Iwasaki, et al., Kodansha (1987)).

The polyclonal antibody according to the present invention can be prepared using a method well known to persons skilled in the art.

The "functional fragment" according to the present invention means a part of an antibody (a partial fragment), which specifically recognizes the protein according to the present invention. Specific examples of such a functional fragment include Fab, Fab', F(ab')$_2$, a variable region fragment (Fv), disulfide-bonded Fv, and a single-chain antibody (scFv), and a polymer thereof.

Preferred examples of the antibody of the first embodiment according to the present invention include an antibody against a protein comprising the amino acid sequence of SEQ ID NO: 4, or an amino acid sequence of SEQ ID NO: 4 which contains one to several conservative substitutions, and a functional fragment thereof.

Preferred examples of the antibody of the second embodiment according to the present invention include an antibody against a peptide comprising the amino acid sequence of SEQ ID NO: 5, or an amino acid sequence of SEQ ID NO: 5 which contains one to several conservative substitutions, and a functional fragment thereof.

Preferred examples of the antibody of the third embodiment according to the present invention include a monoclonal antibody produced by a hybridoma deposited under FERM BP-10782.

Accordingly, according to the present invention, there is provided a hybridoma (0427-L2-1) deposited with the National Institute of Advanced Industrial Science and Technology, International Patent Organism Depositary (AIST Tsukuba Central 6, Higashi 1-1-1, Tsukuba, Ibaraki, 305-8566, Japan), under the accession No. FERM BP-10782 on Feb. 8, 2007.

The antibody according to the present invention is preferably a monoclonal antibody.

According to the present invention, there is provided a monoclonal antibody cross-reactive with the same antigen as that of the monoclonal antibody produced by the hybridoma according to the present invention.

According to the present invention, there is provided an antibody that can bind to *Pseudomonas aeruginosa*, which is produced by the animal's own immune system in response to the antigen compositions according to the present invention.

[Use of Antibody and Pharmaceutical Composition]
Diseases Associated with *Pseudomonas aeruginosa*

*Pseudomonas aeruginosa* is a pathogen of opportunistic infections which cause lethal consequences with reductions in the resistance of hosts. Moreover, *Pseudomonas aeruginosa* is resistant to antibiotics and is therefore a main causative bacterium of hospital infections. As shown later in examples, it was confirmed that the antibody of the third embodiment according to the present invention has opsonic activity (Example 9). It was also confirmed that antisera according to the present invention actually have protective effect against infections on a *Pseudomonas aeruginosa*-susceptible murine model with macrophage functions reduced by administration of mucin (Example 11), and that the antibody according to the present invention actually has protective effect against infections on a *Pseudomonas aeruginosa*-susceptible murine model with a neutrophil level reduced by administration of Cyclophosphamide monohydrate (Example 12). It was further confirmed that the antibody of the third embodiment according to the present invention actually has protective effect against infections on a multidrug resistant *Pseudomonas aeruginosa*-susceptible murine model (Example 13). Thus, the antibody according to the present invention is useful for the prevention or treatment of diseases associated with *Pseudomonas aeruginosa*.

Examples of the diseases associated with *Pseudomonas aeruginosa* include systemic infectious diseases caused by a *Pseudomonas aeruginosa* infection including a multidrug resistant *Pseudomonas aeruginosa* infection, for example, septicemia, meningitis, and endocarditis. Alternative examples of the diseases associated with *Pseudomonas aeruginosa* include: otitis media and sinusitis in the otolaryngologic field; pneumonia, chronic respiratory tract infection, and catheter infection in the pulmonological field; postoperative peritonitis and postoperative infection in a biliary duct or the like in the surgical field; abscess of eyelid, dacryocystitis, conjunctivitis, corneal ulcer, corneal abscess, panophthalmitis, and orbital infection in the opthalmological field; and urinary tract infections (including complicated urinary tract infection), catheter infection, and abscess around the anus in the urologic field. Further examples thereof include burns (including a serious burn and a burn of the respiratory tract), decubital infection, and cystic fibrosis.

The antibody of the third embodiment according to the present invention is particularly useful in that it is expected to be effective for the prevention or treatment of a multidrug resistant *Pseudomonas aeruginosa* infection which is difficult to treat. It was also confirmed that the antibody of the first embodiment according to the present invention binds to the peptide of the second embodiment according to the present invention (Examples 7 and 8). Therefore, the antibody of the first embodiment according to the present invention can be expected to have the same effect.

According to the present invention, there is provided use of the antibody according to the present invention for producing a preventive agent or therapeutic agent for diseases associated with *Pseudomonas aeruginosa*.

According to the present invention, there is provided a method for preventing or treating diseases associated with *Pseudomonas aeruginosa*, comprising the step of administering a preventively or therapeutically effective amount of the antibody according to the present invention to mammals including a human.

Diagnostic Agent for *Pseudomonas aeruginosa* Infection

As shown later in examples, it was confirmed that the antibody of the first embodiment according to the present invention binds to each of the protein according to the present invention, the peptide of the first embodiment according to the present invention, and the peptide of the second embodiment according to the present invention (Example 7). It was also confirmed that the antibody of the second embodiment according to the present invention binds to the protein according to the present invention and the peptide of the first embodiment according to the present invention (Example 7). It was further confirmed that the antibody of the third embodiment according to the present invention binds to the protein according to the present invention and the peptide of the second embodiment according to the present invention (Example 7). Moreover, it was confirmed that the antibodies of the first to third embodiments according to the present invention bind to the extracellular regions of the PA0427 protein that is exposed on *Pseudomonas aeruginosa* cell surface (Example 8).

These results suggested that the antibody according to the present invention can be used to detect the presence of *Pseudomonas aeruginosa*. Thus, the antibody according to the present invention can be used as a diagnostic agent for a *Pseudomonas aeruginosa* infection.

According to the present invention, there is provided a method for diagnosing a *Pseudomonas aeruginosa* infection using the antibody according to the present invention.

The diagnosis method according to the present invention can be carried out by collecting biological samples such as sputum, a lung lavage fluid, pus, tears, blood, or urine from mammals including a human at risk of a *Pseudomonas aeruginosa* infection, subsequently contacting the collected samples with the antibody according to the present invention, and determining whether or not an antigen-antibody reaction occurs.

Diagnostic Agent Kit for *Pseudomonas aeruginosa* Infection

According to the present invention, there is provided a kit for detecting the presence of *Pseudomonas aeruginosa*, comprising at least the antibody according to the present invention.

The antibody according to the present invention may be labeled. This detection kit detects the presence of *Pseudomonas aeruginosa* by detecting an antigen-antibody reaction.

Thus, the detection kit according to the present invention can further contain various types of reagents for carrying out an antigen-antibody reaction, a secondary antibody used, for example, in ELISA, a chromogenic reagent, a buffer, instructions, and/or an instrument, etc., if desired.

Pharmaceutical Composition

The pharmaceutical composition or agent according to the present invention may be used in the form of a composition comprising the antibody according to the present invention as an active ingredient and preferably containing the purified antibody, and optionally other components, for example, a saline, an aqueous glucose solution, and a phosphate buffer.

The pharmaceutical composition according to the present invention may be formulated as a liquid or freeze-dried form, as necessary. Such a pharmaceutical composition may optionally contain pharmaceutically acceptable carriers, for example, a stabilizer, a preservative, and an isotonic agent.

Examples of the pharmaceutically acceptable carriers can include: mannitol, lactose, saccharose, and human albumin for a freeze-dried preparation; and a saline, water for injections, a phosphate buffer, and aluminum hydroxide for a liquid preparation, but not limited to these.

An administration route may differ depending on the age, body weight, sex, and general health of a recipient, but administration can be carried out by any of oral administration and parenteral administration (e.g., intravenous injection, intraarterial injection, and local administration) routes. Among them, parenteral administration is preferable.

A dose of the pharmaceutical composition differs depending on the age, body weight, sex, and general health of a patient, the severity of a *Pseudomonas aeruginosa* infection, and components of an antibody composition to be administered. A daily dose of the antibody composition according to the present invention is generally 0.1 to 1000 mg/kg of body weight, preferably 1 to 100 mg/kg of body weight, per adult for intravenous injection.

It is preferable that the pharmaceutical composition according to the present invention should be administered in advance to a patient at risk of a *Pseudomonas aeruginosa* infection.

When the pharmaceutical composition is prepared as a diagnostic agent, this diagnostic agent can be obtained in any dosage form by adopting any means suitable for the purpose. For example, ascites, a culture solution containing the antibody of interest, or the purified antibody is measured for its antibody titer and appropriately diluted with PBS (phosphate buffer containing a saline) or the like, and a preservative such as 0.1% sodium azide is then added thereto. Alternatively, the antibody of the present invention adsorbed on latex or the like is also determined for its antibody titer and appropriately diluted, and a preservative is added thereto for use. Such an antibody of the present invention bound with latex particles is one of preferable dosage forms as a diagnostic agent. In this case, appropriate resin materials, for example, polystyrene, polyvinyl toluene, or polybutadiene, are suitable as the latex.

EXAMPLES

Hereinafter, the present invention will be described with reference to examples for promoting understanding of the present invention. However, the present invention is not intended to be limited to these examples.

Example 1

GeneChip® Analysis

GeneChip® expression analysis system (Affymetrix, GeneChip® *P. aeruginosa* genome array) was used as an approach for identifying genes that are expressed in a medium supplemented with human sera. Shake culture was carried out using *Pseudomonas aeruginosa* PAO1 strains (ATCC BAA-47) under 3 different culture conditions, that is, in Luria-Bertani (LB) media (Nacalai Tesque) supplemented with 0%, 20%, and 50% human sera (the final composition of LB media was equal among them) at 37° C. until absorbance at 595 nm reached 1.0. Using RNeasy Protect Bacteria Mini kit (QIAGEN GmbH), total RNA was extracted according to the method described in documents included therewith and quantified using 2100 bioanalyzer (Agilent Technologies). Then, experiments were carried out according to the method described in documents included with GeneChip®. Gene expression data was analyzed using Microarray Suite 5.0 (Affymetrix), and signal and detection were calculated. At this time, correction was carried out such that the average value of signals from all probe sets was 1000. Two independent experiments were carried out.

As a result, a PA4761 protein (DnaK or HSP70), which is a house keeping protein, was determined, under all the culture conditions regardless of the presence or absence of added sera, to be "Present" that indicates that a transcription product was detected, and it was thus shown that the gene is expressed. Moreover, a PA2018 protein (MexY) (J. Bacteriology, 2005, 187, 5341-5346), which is an inner membrane-spanning protein that associates with PA5158 (OpmG) and PA2019 (MexX) proteins so as to constitute drug efflux pumps and is induced by ribosome inhibitors such as tetracycline or aminoglycoside antibiotics, was determined, under these conditions free of these drugs, to be "Absent", and it was thus shown that the gene is not expressed. By contrast, with regard to a PA0427 gene, determination to be "Present" was made under all the conditions regardless of the presence or absence of added sera.

Thus, the PA0427 gene is certainly expressed, and the possibility that its gene product PA0427 protein is constantly present on the bacterial surface was suggested. This suggested that the *Pseudomonas aeruginosa* PA0427 protein is useful as a vaccine component.

Example 2

Analysis of PA0427 Gene in Clinical Isolates

Bacterial strains used were 95 *Pseudomonas aeruginosa* strains (stored in Yokohama Research Lab., Meiji Seika Kaisha) isolated from various types of clinical materials in clinical facilities across Japan, and were subjected to tests. These strains were derived from blood, urine, sputum, pus, pharyngeal mucus, and the like, and their serotypes include group A, B, E, F, G, I, M, etc., based on serological classification according to the decision of the serotyping committee sponsored by Japan *Pseudomonas aeruginosa* Society (1975).

(1) Preparation of Genomic DNA

Each of 95 clinical isolates of *Pseudomonas aeruginosa* was cultured overnight at 37° C. in a Mueller-Hinton medium (Becton Dickinson) and collected by low-speed centrifugation. Using DNeasy Tissue kit (QIAGEN GmbH), genomic DNA was prepared from the obtained bacterial cells according to the method described in documents included therewith.

(2) Amplification of DNA Fragment by the PCR Method

Using the prepared genomic DNA as a template, a region containing the PA0427 gene was amplified by PCR. Specifically, a primer set (SEQ ID NO: 7 and SEQ ID NO: 8) for specifically amplifying the PA0427 gene was designed based on the *Pseudomonas aeruginosa* PAO1 genomic sequence (NCBI accession No. NC_002516 on the database). Using GeneAmp PCR System 9700 (Applied Biosystems), PCR was carried out using Takara ExTaq (Takara Bio) according to instructions included therewith. The DNA fragment thus amplified by PCR was confirmed by agarose gel electrophoresis to have the size of interest (1628 bp).

(3) Analysis of Polynucleotide Sequence Using DNA Sequencer

The PCR product was purified using MultiScreen PCR plate (Millipore Corporation) and then subjected to a sequencing reaction. Primers (SEQ ID NO: 9 to SEQ ID NO: 13) capable of sequencing each PCR product were designed based on the PAO1 genomic sequence (NC_002516). BigDye Terminator v1.1 Cycle Sequencing kit (Applied Biosystems) was used in a sequencing reaction. The sequencing reaction was carried out using GeneAmp PCR System 9700 (Applied Biosystems) according to instructions included therewith. The sequencing reaction product was purified using MultiScreen-HV plate (Millipore Corporation) filled with Sephadex G-50 Fine DNA Grade (Amersham Biosciences AB) swollen with water in advance. Then, the polynucleotide sequence was analyzed using Applied Biosystems 3730 DNA Analyzer (Applied Biosystems).

The polynucleotide sequences in the clinical isolates determined by the analysis were converted to polypeptide sequences, and these polypeptide sequences were compared with those from the PAO1 strain. As a result, 3 mutations were observed in the full-length sequence of the PA0427 protein (Table 1).

However, putative extracellular regions (SEQ ID NO: 5 and SEQ ID NO: 6) predicted by the present inventors based on secondary structure and three-dimensional structure information about the *Pseudomonas aeruginosa* PA0427 protein (J. Biol. Chem., 2004, 279, 52816-52819) and three-dimensional structure information about an *E. coli* TolC protein (Nature, 2000, 405, 914-919), were confirmed to have no detectable mutation. This suggested that the *Pseudomonas aeruginosa* PA0427 protein is useful as a "*Pseudomonas aeruginosa* common antigen."

TABLE 1

Mutation pattern of the PA0427 protein in clinical isolates

| Pattern | Amino acid No. | | | The number of strains |
|---|---|---|---|---|
| | 72 | 156 | 474 | |
| PAO1 type | V | A | Q | 90 |
| 1 | L | — | — | 3 |

TABLE 1-continued

Mutation pattern of the PA0427 protein in clinical isolates

| Pattern | Amino acid No. | | | The number of strains |
| --- | --- | --- | --- | --- |
| | 72 | 156 | 474 | |
| 2 | — | T | — | 1 |
| 3 | — | — | R | 1 |
| Total | | | | 95 |

"—" represents the same amino acid as that in the PA01 strain

Example 3

Cloning of the PA0427 Gene DNA Fragment

A DNA fragment (SEQ ID NO: 2) from nucleotides 340 to 1017 in 1458 nucleotides as an amino acid coding region of the *Pseudomonas aeruginosa* PA0427 gene (SEQ ID NO: 1) was cloned using a vector pIVEX2.4d (Roche Diagnostics) and incorporated into an expression vector pET15b (Novagen) by the following method.

Based on structure analysis information about an *E. coli* TolC protein (Nature, 2000, 9405, 914-919) homologous to the PA0427 protein, it was estimated that nucleotide sequences of nucleotides 1 to 339 and 1018 to 1458 in the amino acid coding region encode a cell surface-unexposed region. Thus, these nucleotide sequences were excluded from cloning.

The DNA fragment to be cloned was amplified from the *Pseudomonas aeruginosa* PAO1 genomic DNA by PCR (DNA Thermal Cycler 480; Perkin-Elmer). Pyrobest (Takara Shuzo) was used as DNA polymerase. A reaction solution was supplemented with 5% dimethyl sulfoxide. Primers (SEQ ID NO: 14 and SEQ ID NO: 15) containing nucleotides for adding restriction sites NcoI (CCATGG) and PstI (CTGCAG) and a stop codon were used as PCR primers.

PCR temperature conditions involved heating at 94° C. for 2 minutes and subsequent 30 cycles consisting of 94° C.-30 seconds, 60° C.-1 minute, and 72° C.-2 minutes. The PCR product was purified using GenElute PCR DNA Purification Kit (Sigma), and the purified product was digested with NcoI and PstI (both New England Biolabs). pIVEX2.4d was digested with NcoI and PstI. These DNA fragments were electrophoresed on agarose gel, and extracted and purified using QIAquick Gel Extraction Kit (Qiagen). The PCR product and pIVEX2.4d thus digested with NcoI-PstI were ligated using T4 DNA ligase (Invitrogen), and *E. coli* DH5α strains (Competent High DH5α, Toyobo) were transformed with the ligation product. The pIVEX2.4d plasmid in which the PA0427 gene fragment had been incorporated (pIVEX-PA0427-1) was purified using QIAprep Spin Miniprep Kit (Qiagen), and the nucleotide sequence of the insert was confirmed (3730 DNA Analyzer, Applied Biosystems/HITCHI) by a cycle sequencing reaction using BigDye Terminator v1.1 Cycle Sequencing Kit (Applied Biosystems).

Figure 1:
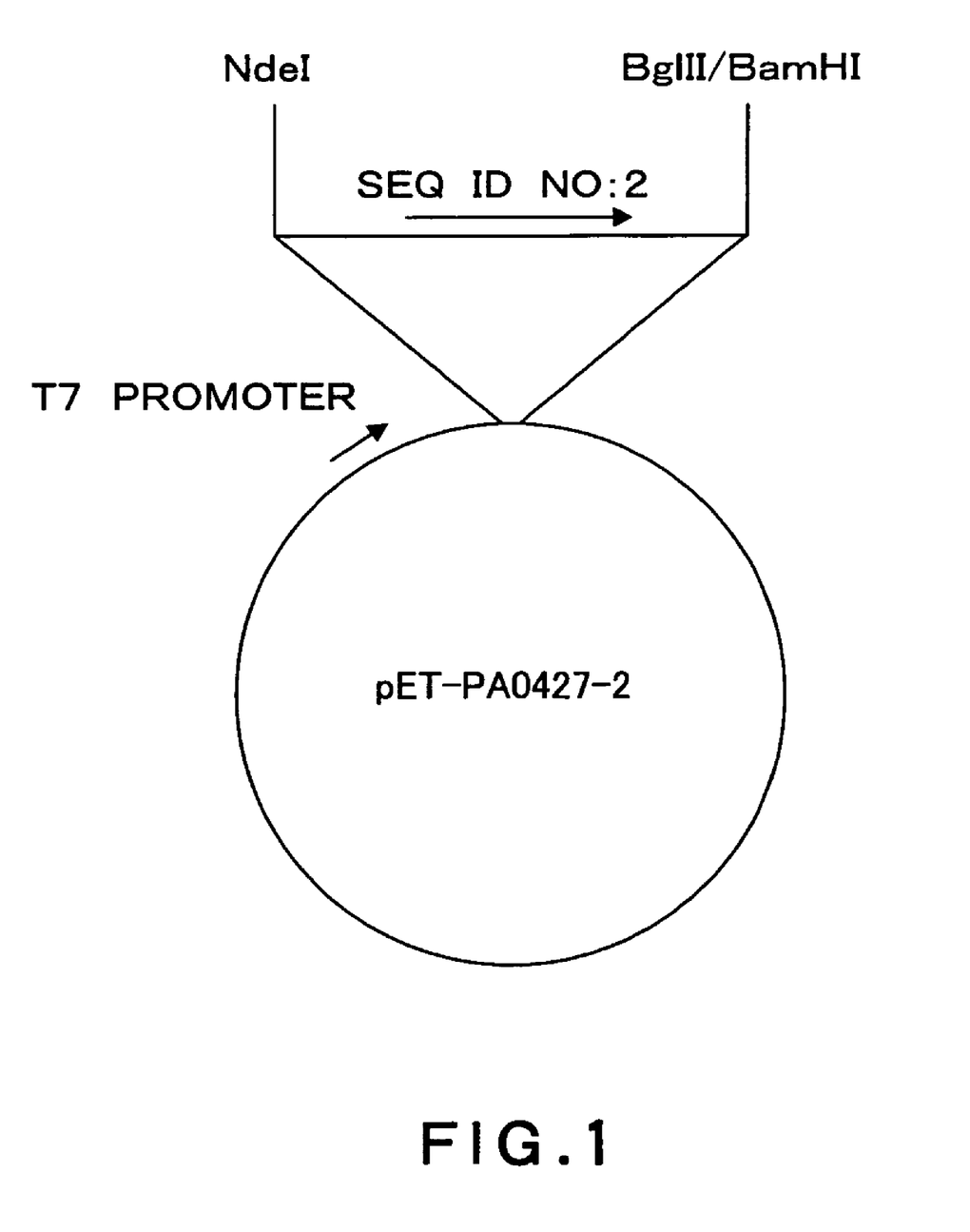
FIG. 1 shows a pET15b plasmid (pET-PA0427-2).

Next, pET15b was digested with NdeI (New England Biolabs) and BamHI (Toyobo). Moreover, using pIVEX-PA0427-1 as a template, the insert fragment was amplified using a PCR primer (SEQ ID NO: 16) pairing with a region positioned upstream of the insert and a PCR primer (SEQ ID NO: 17) containing nucleotides for adding a restriction site BglII (AGATCT) and a stop codon, and the PCR product was digested with NdeI immediately upstream of the NcoI site and with BglII (Toyobo). Protruding ends after such digestions with BamHI and with BglII are complementary to each other. Therefore, these digested DNA fragments were ligated. *E. coli* was transformed with the ligation product, so as to obtain the pET15b plasmid in which the PA0427 gene fragment had been incorporated (pET-PA0427-2) (FIG. 1).

Example 4

Expression and Purification of the PA0427 Recombinant Protein

*E. coli* BL21 (DE3) strains in which a T7 RNA polymerase gene has been incorporated, and a pET vector expression system (Novagen) having a T7 promoter were used in expression of a recombinant protein. The *E. coli* expression vector pET-PA0427-2 is a plasmid that encodes the PA0427 partial protein, in which His-tag (6 consecutive histidines) has been fused downstream of the T7 promoter (see Example 3). The BL21 (DE3) strains were treated with calcium chloride (see Molecular Cloning 2nd ed., Sambrook et al. (1989)) and transformed with pET-PA0427-2. The transformants were cultured overnight in an LB medium containing 50 μg/ml ampicillin, and they were suspended (200 fold diluted) in a fresh medium and cultured at 37° C. for 4 hours. Then, expression was induced by addition of IPTG at a final concentration of 0.5 mM, and culture was continued for additional 3 hours. The cells were collected by centrifugation and frozen at −20° C. The cells were dissolved in B-PER Bacterial Protein Extraction Reagent (Pierce), and an insoluble fraction containing the expressed protein was collected and treated with lysozyme (egg-white lysozyme, Seikagaku Corporation) at a final concentration of 100 μg/ml, followed by washing with a Dulbecco's phosphate-buffered saline (PBS) supplemented with 1% Triton X-100.

Ni chelate chromatography using the His-tag was used in protein purification. The insoluble protein thus expressed and prepared was solubilized with a dissolution buffer (PBS supplemented with 8 M urea, 5 mM imidazole, 200 mM NaCl, and 0.05% NP-40). The dissolved protein was bound to Ni-NTA Agarose (Qiagen) and washed with 40 volumes of a dissolution buffer. The protein was further washed with 40 volumes of a wash buffer (having the same composition as that of the dissolution buffer except for NP-40). Then, the His-tag-fused protein was eluted with an elution buffer (PBS supplemented with 8 M urea, 300 mM imidazole, and 200 mM NaCl), followed by collection.

As a result, 2.0 mg of the protein was finally obtained by the culture of 115 ml of *E. coli*.

Example 5

Immunization with Antigen and Preparation of Antisera

*Pseudomonas aeruginosa* PA103 strains (ATCC29260) were cultured overnight at 37° C. on a Mueller-Hinton agar medium. A few colonies were suspended in an LB medium and then shake-cultured overnight at 37° C., and they were washed with PBS, followed by resuspension. Then, inactivation treatment was carried out for 24 hours or longer by addition of 1% formalin, and the strains thus inactivated (hereinafter, occasionally referred to as "formalin-inactivated PA103 strains") were used.

For use in immunization, the PA0427 recombinant protein was dissolved in an 8 M urea solution, resulting in a concentration of 100 μg/ml.

The amino acid sequences of the extracellular regions in the PA0427 protein were estimated by the present inventors based on secondary structure and three-dimensional structure information about the *Pseudomonas aeruginosa* PA0427 protein (J. Biol. Chem., 2004, 279, 52816-52819) and three-dimensional structure information about an *E. coli* TolC protein (Nature, 2000, 405, 914-919).

Peptides containing the estimated amino acid sequences (SEQ ID NO: 5 and SEQ ID NO: 6) were synthesized by a solid-phase synthesis method using Fmoc. A peptide consisting of the amino acid sequence of SEQ ID NO: 5 (hereinafter, occasionally referred to as "0427L1") was synthesized as the synthetic peptide containing the amino acid sequence of SEQ ID NO: 5. A peptide in which a cysteine residue was added to the carboxyl terminal of the amino acid sequence of SEQ ID NO: 6 (hereinafter, occasionally referred to as "0427L2Q") was synthesized (SEQ ID NO: 18) as the synthetic peptide containing the amino acid sequence of SEQ ID NO: 6. [M+1] m/z 1592.94 (calculated value: m/z 1591.77) was observed by mass spectrometry in the synthetic peptide 0427L1 consisting of the amino acid sequence of SEQ ID NO: 5, and a peak with an area ratio of 71.1% at a retention time of 13.199 minutes was given by HPLC analysis for the synthetic peptide. Alternatively, [M+1] m/z 1615.51 (calculated value: m/z 1613.84) was given by mass spectrometry for the synthetic peptide 0427L2Q containing the amino acid sequence of SEQ ID NO: 6, and a peak with an area ratio of 74.7% at a retention time of 16.75 minutes was observed by HPLC analysis for the synthetic peptide. Each of the synthetic peptides was coupled to KLH via a spacer, so as to prepare KLH-conjugated peptides, and these KLH-conjugated peptides were designated as 0427L1-KLH and 0427L2Q-KLH, respectively. DMS (Dimethyl suberimide.2HCl, Pierce, catalog No. 20700) or sulfo-MBS (m-Maleimidobenzoyl-N-hydroxysulfosuccinimide ester, Pierce, catalog No. 22312) was used as the spacer. Synthesis of the peptides was entrusted to Thermo Electron.

For immunization, 20 µg/animal each of the formalin-inactivated PA103 strain, the PA0427 recombinant protein, and the KLH-conjugated peptides was used in combination with an adjuvant. In an administration method to an animal, a male BN rat (purchased from Charles River Laboratories, Japan) was subcutaneously or intramuscularly immunized with 6 shots in total, the first shot in combination with a complete Freund adjuvant and the subsequent shots in combination with an incomplete adjuvant, at 2-week intervals. One week after the final immunization, whole blood was collected from the abdominal aorta, and it was left at room temperature for 1 hour and then centrifuged at 1500 G for 20 minutes, so as to obtain a supernatant having approximately 5 mL/rat of sera.

Example 6

Purification of the IgG Fraction from Antisera

An IgG fraction was purified from the rat antisera according to, for example, the method of McCauley R & Racker, E; Molecular and Cellular Biochemistry 1, 73-81 (1973). An ice-cold saturated ammonium sulfate solution (pH 8) was added to prepare a 43 (v/v) % suspension, and the obtained suspension was stirred at room temperature for 15 minutes. Precipitates were collected by centrifugation at 10,000×g for 20 minutes and dissolved in a 10 mM potassium phosphate buffer (pH 8) supplemented with 10% glycerol. Then, precipitates were deposited again by addition of an ice-cold saturated ammonium sulfate solution (pH 8) to prepare a 50 (v/v) % solution, so as to complete 2 washes. The precipitates were dissolved in a 10 mM potassium phosphate buffer (pH 8) supplemented with 10% glycerol, and subsequently dialyzed overnight against the buffer. The dialysate was centrifuged and then applied to anion-exchange chromatography (DEAE-Toyopearl 650M (TOSOH)). The pass-through volume was collected as an IgG fraction by measuring ultraviolet absorption at 280 nm. The collected fraction was concentrated using Amicon Ultra-15 (Millipore), and the buffer was finally exchanged with a PBS (−) solution, so as to obtain a final sample. 14.5 mg of a protein was collected as an IgG fraction by purification from 5 ml of the PA0427 recombinant protein-immunized rat antisera, and this fraction was designated as anti-PA0427 IgG. The protein was quantified according to DC Protein Assay (Bio-Rad) based on the Lowry method, and IgG purity was evaluated by SDS-PAGE.

For example, the method of Harlow & Lane, 288-318, Chapter 8, Antibodies, A Laboratory Manual, Cold Spring Harbor (1988) was used as a simple alternative method. To a supernatant of the rat antisera from which insoluble matter had been removed by centrifugation at 10,000×g for 20 minutes, 2 volumes of 60 mM sodium acetate (pH 4.0) were added, and the pH was then adjusted to 4.8 with 1 N hydrochloric acid. A 0.06 volume of caprylic acid relative to the antisera was gradually added at room temperature, and the mixture was stirred for 30 minutes, so as to produce insoluble matter. Precipitates were removed by centrifugation at 13,000×g for 10 minutes, and the resulting solution was then passed through a 0.45-µm filter. The obtained sample was concentrated using Amicon Ultra-15 (Millipore), and the buffer was finally exchanged with a PBS (−) solution, so as to obtain a final sample. 68 and 27 mg of proteins were collected as an IgG fraction by purification from 30 ml each of the KLH-conjugated peptide (i.e., 0427L1-KLH and 0427L2Q-KLH)-immunized rat sera, respectively, according to this method, and these fractions were designated as anti-0427L1 IgG and anti-0427L2Q IgG, respectively. The proteins were quantified according to DC Protein Assay (Bio-Rad) based on the Lowry method, and IgG purity was evaluated by SDS-PAGE.

Example 7

ELISA Test

In order to detect an antibody that binds to the PA0427 recombinant protein or each of the synthetic peptides 0427L1 and 0427L2Q by the ELISA method, the PA0427 recombinant protein was dissolved in PBS supplemented with 8 M urea, and each of the synthetic peptides 0427L1 and 0427L2Q was dissolved in a carbonate buffer (0.15% Na2CO3, 0.3% NaHCO3). The protein or the peptide was placed in a 96-well ELISA plate (MaxiSorp Type, NUNC). The plate was left overnight at 4° C., so as to cause immobilization. The plate was washed with PBS and blocked with PBS supplemented with 0.5% BSA. Then, each purified IgG fraction obtained in Example 6 was added as a sample to the wells and allowed to react at room temperature. The plate was washed with PBS containing 0.05% Tween 20. Then, a secondary antibody (peroxidase-labeled goat anti-rat IgG antibody, 10000 fold diluted, Sigma) was added thereto and allowed to react therewith at room temperature, and the plate was then washed. An enzyme reaction was carried out by addition of a chromogenic substrate (TMB Microwell Peroxidase Substrate System, KPL) and then terminated with a 1 M phosphoric acid solution. Absorbance at 450 nm was measured.

As a result, when the PA0427 recombinant protein was immobilized, the absorbance of the anti-PA0427 IgG fraction was 0.961. By contrast, the absorbance of a negative control sham rat IgG fraction was 0.080. This indicates that the antibody (IgG) that binds to the PA0427 recombinant protein used as an antigen is contained in the anti-PA0427 IgG fraction. Moreover, the absorbances of the anti-PA0427L1 IgG and anti-PA0427L2Q IgG fractions were 0.353 and 0.751, respectively. This indicates that the antibody (IgG) that binds to the PA0427 recombinant protein is also contained in these fractions.

Alternatively, when the synthetic peptide 0427L1 was immobilized, the absorbance of the anti-PA0427 IgG fraction was 0.750. By contrast, the absorbance of a negative control sham rat IgG fraction was 0.015. This indicates that the antibody (IgG) that binds to the synthetic peptide 0427L1 consisting of the amino acid sequence (SEQ ID NO: 5), one of the putative extracellular regions, is contained in the anti-PA0427 IgG fraction. The absorbance of the anti-PA0427L1 IgG fraction was 0.117, and this indicates that the antibody (IgG) that binds to the synthetic peptide 0427L1 is also contained in this fraction. By contrast, the absorbance of the anti-PA0427L2Q IgG fraction was 0.034, and this indicates that the antibody (IgG) that binds to the synthetic peptide 0427L1 is not contained in this fraction.

Furthermore, when the synthetic peptide 0427L2Q was immobilized, the absorbance of the anti-PA0427 IgG fraction was 0.569. By contrast, the absorbance of a negative control sham rat IgG fraction was 0.063. This indicates that the antibody (IgG) that binds to the synthetic peptide 0427L2Q containing the amino acid sequence (SEQ ID NO: 6), one of the putative extracellular regions, is contained in the anti-PA0427 IgG fraction. The absorbance of the anti-PA0427L2Q IgG was 0.361, and this indicates that the antibody (IgG) that binds to the synthetic peptide 0427L2Q is also contained in this fraction. By contrast, the absorbance of the anti-PA0427L1 IgG fraction was 0.101, and this indicates that the antibody (IgG) that binds to the synthetic peptide 0427L2Q is not contained in this fraction.

Example 8

Whole Cell ELISA Test

For whole cell ELISA, a bacterial solution of PA103 strains cultured overnight in an LB medium was dispensed at a concentration of 100 μL/well into a 96-well ELISA plate (MaxiSorp Type, NUNC), followed by immobilization at 4° C. for 1 hour. The plate was then washed with a wash buffer (TBS containing 0.05% Tween 20) and blocked with a blocking buffer (TBS containing 2% bovine serum albumin). Thereafter, each purified IgG fraction obtained in Example 6 was added to the wells and allowed to react at 37° C. for 1 hour. After washing, a secondary antibody (peroxidase-labeled goat anti-rat IgG antibody, 5000 fold diluted, Sigma) was added thereto and allowed to react therewith at room temperature for 1 hour, and the plate was then washed. An enzyme reaction was carried out in the dark by addition of a chromogenic substrate (TMB Microwell Peroxidase substrate System, KPL) and then terminated with a 1 M phosphoric acid solution. Absorbance at 450 nm was measured.

As a result, the absorbance of the anti-PA0427 IgG was 0.713, whereas the absorbance of negative control sham rat IgG was 0.240. This indicates that the antibody (IgG) that recognizes the extracellular region of the PA0427 protein that is exposed on *Pseudomonas aeruginosa* cell surface is contained in the anti-PA0427 IgG. Alternatively, the absorbances of the anti-PA0427L1 IgG and the anti-PA0427L2Q IgG were 0.555 and 0.596, respectively. This indicates that the antibody (IgG) that recognizes the extracellular region of the PA0427 protein that is exposed on *Pseudomonas aeruginosa* cell surface is also contained in these samples.

Example 9

Opsonic Activity Confirmation Test

The purified IgG fraction (anti-0427L2Q IgG) obtained from the 0427L2Q-KLH-immunized rat sera in Example 6 was studied for its opsonic activity using the phagocytosis of *Pseudomonas aeruginosa* by murine neutrophils as an index.

An 8% casein solution was intraperitoneally administered to a male BALB/c mouse (purchased from Charles River Laboratories, Japan). Six hours later, peritoneal cells were collected. The peritoneal cells were washed by centrifugation and then suspended at a concentration of $2 \times 10^6$ cells/mL in an RPMI-1640 medium (Gibco). The cells and fluorescently labeled *P. aeruginosa* PA103 strains treated with 4% paraformaldehyde were subjected to mixed culture at a ratio of 25:1 for 1.5 hours in the presence of a rat complement (ICN Biomedicals) and the anti-0427L2Q IgG or IgG purified from control rat sera obtained by administration of only an adjuvant. After such culture, phagocytized *P. aeruginosa* was measured with a flow cytometer (Epics LX II, Coulter). A neutrophil region was gated, and the fluorescence intensities of 10,000 cells were measured. The average fluorescence intensity was used as an index for opsonic activity.

As a result, the average fluorescence intensities of the neutrophils cultured with *P. aeruginosa* in the presence of 100 μg/mL and 200 μg/mL anti-0427L2Q IgG were 0.39 and 0.52, respectively, whereas the average fluorescence intensities of the neutrophils cultured with *P. aeruginosa* in the presence of 100 μg/mL and 200 μg/mL control IgG were 0.36 and 0.41, respectively, demonstrating the opsonic activity of the anti-0427L2Q IgG.

Example 10

Preparation of Monoclonal Antibody (MAb)

One week after the first immunization in Example 5 with the KLH-conjugated peptide 0427L2Q-KLH containing the putative extracellular region (SEQ ID NO: 6) predicted by the present inventors based on secondary structure and three-dimensional structure information about the *Pseudomonas aeruginosa* PA0427 protein (J. Biol. Chem., 2004, 279, 52816-52819) and three-dimensional structure information about an *E. coli* TolC protein (Nature, 2000, 405, 914-919), booster was carried out in combination with an incomplete adjuvant. Three days thereafter, the subgenual lymph nodes were aseptically extracted under anesthesia. The obtained lymph nodes were washed with an RPMI-1640 medium (Gibco), and they were then inserted between the frosted portions of slide glasses and crushed, so as to obtain a lymph node cell test sample as fine small pieces. The obtained lymph node cells were washed by centrifugation at 1000 rpm for 5 minutes using an RPMI-1640 medium. On the other hand, myeloma cells (P3X63Ag8U1 cells) were cultured in advance at 5% $CO_2$, relative humidity of 100%, and 37° C. in an RPMI-1640 medium containing 10% FCS (fetal bovine serum), and the thus cultured myeloma cells during the exponential phase of growth were washed by centrifugation using an RPMI-1640 medium and mixed with the aforementioned lymph node cells, such that a ratio of the number of the lymph node cells to the number of the myeloma cells became approximately 4:1. The mixed cells were centrifuged at 1000 rpm for 5 minutes. The supernatant was discarded, and the cells were sufficiently loosened. To the centrifuge tube containing the cells, 1 mL of a solution consisting of 2 g of polyethylene glycol (M.W. 1000, Wako Pure Chemical Industries), 2 mL of an RPMI-1640 medium, and 0.2 mL of DMSO (Nacalai Tesque) was gently added. The cells were mixed by slowly rotating the centrifuge tube. One minute later, the centrifuge tube was slowly rotated, while 15 mL of an RPMI-1640 medium was added thereto over 3 minutes. The cells were centrifuged at 1000 rpm for 5 minutes. Then, the supernatant was discarded, and the cells were sufficiently loosened. Then, the cells were suspended in 50 mL of an HT medium (Gibco) and cultured overnight. Thereafter, the cells were collected by centrifugation at 1000 rpm for 10 minutes and suspended in 10 mL of an RPMI medium, and the cell solution was then added to a bottle containing 90 mL of a methylcellulose HAT selection medium (Stem Cell Technologies) and sufficiently mixed. The mixed cells in the methylcellulose medium were seeded at a concentration of 10 mL/dish to 9-cm dishes. The cells were cultured at 5% $CO_2$, relative humidity of 100%, and 37° C. Approximately 10 to 14 days later, colonies of hybridomas grown on the methylcellulose medium were observed. These colonies were picked up and further cultured in a 96-well microplate for a few days.

(1) Screening of Antibody of Interest

An antibody that binds to the PA0427 recombinant protein or the synthetic peptide (SEQ ID NO: 18) containing the putative extracellular region (SEQ ID NO: 6) was detected by the ELISA described in Example 7. Moreover, an antibody that binds to the cell surface of *Pseudomonas aeruginosa* was detected by the whole cell ELISA described in Example 8.

(2) Cloning of Cells Producing Antibody of Interest

The hybridomas determined by screening to produce the antibody of interest were adjusted to 1 hybridoma/0.2 mL using a 10% FCS/HT (Gibco) medium containing 5% BM-Condimed H1 Hybridoma Cloning Supplement (Roche Diagnostics), and dispensed at a concentration of 0.2 mL/well to the wells of a 96-well plate, followed by culture. One to two weeks later, clones were analyzed by the method described in the paragraph for screening, so as select monoclones producing the antibody of interest. As a result, a hybridoma deposited with the National Institute of Advanced Industrial Science and Technology, International Patent Organism Depositary under the accession No. FERM BP-10782 was obtained.

(3) In Vitro Culture of Cells and Production of MAb

The clones of interest sufficiently proliferated in the 96-well microplate were scaled up in stages in a 24-well plate, a 50-mL flask, and a 250-mL flask and cultured in a 10% FCS-RPMI medium. MAb produced in the culture supernatant of the cells thus obtained was detected by the ELISA described in Example 7.

In such ELISA for detecting binding to the well on which each of no peptide, the synthetic peptide 0427L1 (SEQ ID NO: 5), and the synthetic peptide 0427L2Q (SEQ ID NO: 18) had been adsorbed, the absorbances were 0.049, 0.049, and 0.610, respectively in the culture supernatant of the hybridoma deposited with the National Institute of Advanced Industrial Science and Technology, International Patent Organism Depositary under the accession No. FERM BP-10782, demonstrating that the MAb that specifically binds to the synthetic peptide 0427L2Q (SEQ ID NO: 18) is produced.

(4) In Vivo Cell Propagation in Ascites and Production of MAb

The hybridoma deposited with the National Institute of Advanced Industrial Science and Technology, International Patent Organism Depositary under the accession No. FERM BP-10782 was intraperitoneally administered at a concentration of $1\times10^7$ hybridomas/mouse to BALB/c-nu/nu mice (purchased from Charles River Laboratories, Japan). One to two weeks later, the ascites was collected. MAb contained in the ascites was purified by the method described in Example 6, and the obtained purified IgG fraction was designated as anti-0427L2Q(48-5) IgG. The IgG subclass of this rat MAb was determined to be IgG2a and κ for heavy and light chains, respectively, using a monoclonal antibody isotyping kit (RMT1, Dainippon Pharmaceutical).

The antibody that binds to the PA0427 recombinant protein or the synthetic peptide (SEQ ID NO: 18) was detected by the ELISA described in Example 7.

As a result, in such ELISA for detecting binding to the well on which the PA0427 recombinant protein had been adsorbed, the absorbance of the anti-0427L2Q(48-5) was 0.906, whereas the absorbance of negative control sham rat IgG was 0.080, demonstrating that the MAb that binds to the protein is produced.

Moreover, in the ELISA for detecting binding to the well on which the synthetic peptide 0427L2Q (SEQ ID NO: 18) had been adsorbed, the absorbance of the anti-0427L2Q(48-5) was 0.585, whereas the absorbance of negative control sham rat IgG was 0.063, demonstrating that the MAb that binds to the peptide is produced.

Example 11

Ability of PA0427 Recombinant Protein-Immunized Rat Sera to Defend Against PA103 Strain Systemic Infection in Normal Mice In evaluation with systemically infected models of normal mice, PA103 strains suspended in 500 µl of a saline containing 5% mucin were intraperitoneally inoculated at a dose of $7.0\times10^4$ cfu/mouse (14 $LD_{50}$) to 4-week-old male CD-1 mice (purchased from Charles River Laboratories, Japan). Immediately thereafter, the serum sample 5 fold diluted with a saline was administered at a dose of 10 ml/kg from the caudal vein. Seven days later, protective activity against the infection was determined based on survival.

As a result, 5 out of 7 mice died in a group to which negative control sham rat sera obtained by administration of only an adjuvant had been administered, and the remaining 2 mice survived. By contrast, all mice survived in the group to which the formalin-inactivated PA103 strain-immunized rat sera obtained in Example 5 had been administered. It was thus confirmed that the formalin-inactivated PA103 strain-immunized rat sera have protective activity against the infection. Under this condition, 6 out of 7 mice survived in the group to which the PA0427 recombinant protein-immunized rat sera obtained in Example 5 had been administered. It was thus confirmed that the PA0427 recombinant protein-immunized rat sera have protective activity against the infection.

Example 12

Ability of PA0427 Recombinant Protein-Immunized Rat Sera and Purified IgG Fractions to Defend Against PA103 Strain Systemic Infection in Neutropenic Mice In evaluation with systemically infected models of neutropenic mice, 12.5 mg/mL (saline) of cyclophosphamide (hereinafter referred to as CY, Sigma-Aldrich) was prepared and intraperitoneally administered at a dose of 125 mg/kg to 4-week-old male CD-1 mice on day −5, −2, and 0 (3 doses in total), so as to reduce a neutrophil level in peripheral blood. Then, PA103 strains suspended in 250 µl of a saline were intraperitoneally inoculated at a dose of $1.0 \times 10^5$ cfu/mouse (74 $LD_{50}$) to the mice. Immediately thereafter, each sample (the sera were 5 fold diluted with a saline, and each of the 5 purified IgG fractions was adjusted to 2.5 mg/mL with a saline) was administered at a dose of 10 or 20 mL/kg from the caudal vein. Seven days later, protective activity against the infection was determined based on survival.

As a result, when the rat sera were used as a sample, all mice died in a group to which negative control sham rat sera obtained by administration of only an adjuvant had been administered. By contrast, all mice survived in the group to which the formalin-inactivated PA103 strain-immunized rat sera obtained in Example 5 had been administered. It was thus confirmed that the formalin-inactivated PA103 strain-immunized rat sera have protective activity against the infection. Under this condition, 5 out of 7 mice survived in the group to which the PA0427 recombinant protein-immunized rat sera obtained in Example 5 had been administered. It was thus confirmed that the PA0427 recombinant protein-immunized rat sera have protective activity against the infection.

Alternatively, when the purified IgG fractions were used as a sample (0.5 mg/mouse), 6 out of 7 mice died in a negative control sham rat IgG-administered group, and the remaining 1 mouse survived. By contrast, 5 out of 7 mice survived in the group to which the anti-PA103 IgG obtained from the formalin-inactivated PA103 strain-immunized rat sera had been administered. It was thus confirmed that the anti-PA103 IgG has protective activity against the infection. Under this condition, 5 out of 7 mice survived in the group to which the anti-0427L1 IgG obtained in Example 6 had been administered. It was thus confirmed that the anti-0427L1 IgG has protective activity against the infection. Moreover, 4 out of 7 mice survived in the group to which the anti-0427L2Q IgG obtained in Example 6 had been administered. It was thus confirmed that the anti-0427L2Q IgG has protective activity against the infection. Furthermore, 4 out of 7 mice were survived in the group to which the anti-0427L2Q (48-5) IgG as rat MAb obtained in Example 10 had been administered. It was thus confirmed that the anti-0427L2Q (48-5) IgG has protective activity against the infection.

Example 13

Ability of Purified IgG Fractions to Defend Against Multidrug Resistant *Pseudomonas aeruginosa* Systemic Infection in Neutropenic Mice The minimum inhibitory concentrations of various types of antimicrobial agents for multidrug resistant *Pseudomonas aeruginosa* MSC06120 strains were imipenem: 32 µg/ml, amikacin: 64 µg/ml, and ciprofloxacin: >256 µg/ml. In evaluation with systemically infected models of neutropenic mice using the strains, 12.5 mg/mL (saline) of CY was prepared and intraperitoneally administered at a dose of 125 mg/kg to 4-week-old male CD-1 mice on day −5, −2, and 0 (3 doses in total), so as to reduce a neutrophil level in peripheral blood. Then, MSC06120 strains suspended in 250 µl of a saline were intraperitoneally inoculated at a dose of $0.925 \times 10^5$ cfu/mouse (8.3 $LD_{50}$) to the mice. Immediately thereafter, each purified IgG sample was administered at a dose of 20 mL/kg (0.5 mg/mouse) from the caudal vein. Seven days later, protective activity against the infection was determined based on survival.

As a result, 4 out of 7 mice died in a negative control sham rat IgG-administered group, and the remaining 3 mice survived. By contrast, 6 out of 7 mice survived in the group to which the anti-PA103 IgG obtained from the formalin-inactivated PA103 strain-immunized rat sera had been administered. It was thus confirmed that the anti-PA103 IgG has protective activity against the infection. Under this condition, 5 out of 7 mice survived in the group to which the anti-0427L2Q IgG obtained in Example 6 had been administered. It was thus confirmed that the anti-0427L2Q IgG has protective activity against the infection.

The invention claimed is:

1. A method for prophylactically treating or treating a disease associated with *Pseudomonas aeruginosa*, comprising administering an effective amount of an antibody or fragment thereof which specifically binds to a peptide selected from the group consisting of (i) a peptide consisting of the amino acid sequence of SEQ ID NO: 6, (ii) a peptide consisting of an amino acid sequence of SEQ ID NO: 6 which contains one to two conservative substitutions, and (iii) a peptide consisting of an amino acid sequence of SEQ ID NO: 6 and having a single amino acid added to the end thereof, the peptide being functionally equivalent to a peptide consisting of the amino acid sequence of SEQ ID NO: 6, to a mammal including a human, wherein the disease associated with *Pseudomonas aeruginosa* is selected from the group consisting of a systematic infectious disease, an otolaryngologic infectious disease, a pulmonological infectious disease, a surgical infectious disease, an opthalmological infectious disease, and an urinary tract infection.

2. The method according to claim 1, wherein the antibody or fragment thereof also specifically binds to a peptide selected from the group consisting of (i) a peptide consisting of the amino acid sequence of SEQ ID NO: 5, and (ii) a peptide consisting of the amino acid sequence of SEQ ID NO: 5 which contains one to two conservative substitutions.

3. The method according to claim 1, wherein the antibody is produced by a hybridoma deposited under accession No. FERM BP-10782.

4. The method according to claim 1, wherein the peptide comprises the amino acid sequence of SEQ ID NO: 18.

5. The method according to claim 1, wherein the antibody is a monoclonal antibody.

6. The method according to claim 1, wherein the antibody is a monoclonal antibody cross-reactive with the same antigen as that of the monoclonal antibody produced by a hybridoma deposited under accession No. FERM BP-10782.

7. The method according to claim 1, wherein the systemic infectious disease is selected from septicemia, meningitis, and endocarditis; the otolaryngologic infectious disease is selected from otitis media and sinusitis; the pulmonological infectious disease is selected from pneumonia and chronic respiratory tract infection, the surgical infectious disease is selected from postoperative peritonitis, postoperative infection and burns; and the opthalmological infectious disease is selected from corneal ulcer and corneal abscess.

* * * * *